United States Patent
Carson et al.

(10) Patent No.: US 6,210,917 B1
(45) Date of Patent: *Apr. 3, 2001

(54) METHOD FOR SUPPRESSING MULTIPLE DRUG RESISTANCE IN CANCER CELLS

(75) Inventors: Dennis A. Carson, Del Mar; Carlos J. Carrera, San Diego, both of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/956,657

(22) Filed: Oct. 23, 1997

Related U.S. Application Data (63) Continuation-in-part of application No. 08/612,542, filed on Mar. 8, 1996, now Pat. No. 5,840,505, and a continuation-in-part of application No. 08/176,855, filed on Dec. 29, 1993, now abandoned.

(51) Int. Cl.[7] ................. C12Q 1/34; C12Q 1/46

(52) U.S. Cl. ................. 435/18; 435/4; 435/21; 435/29; 435/15; 435/24; 435/23; 435/69.2; 435/68.1; 435/172.2; 536/1.1; 536/24.32; 536/24.31

(58) Field of Search ................. 435/18, 4, 21, 435/29, 15, 24, 23, 69.2, 68.1, 172.2; 536/1.11, 1.1, 24.32, 24.31; 514/45

(56) References Cited

U.S. PATENT DOCUMENTS

| | | | |
|---|---|---|---|
| 4,687,733 | * 8/1987 | Trewyn et al. | 435/18 |
| 4,792,520 | 12/1988 | Stambrook et al. | 435/18 |
| 4,822,736 | 4/1989 | Kellems et al. | 435/18 |
| 5,030,623 | * 7/1991 | Gruber | 514/45 |
| 5,118,601 | * 6/1992 | Gruber | 435/29 |

OTHER PUBLICATIONS

Cottom, H.B., et al., "New Adenosine Kinase Inhibitors with Oral Anti–Inflammatory Activity: Synthesis and Biological Evaluation," *J. of Medicinal Chemistry* (1993) Oct.; 36(22):3424–3430.

Lin, B.B., et al., "Regulation of Adenosine Kinase by Adenosine Analogs," *Molecular Pharmacology* (1988) Oct.; 34(4):501–505.

Bone, R., et al., "Inhibition of Adenosine and Thymidylate Kinases by Bisubstrate Analogs," *J. Biol. Chemistry* (1986) Dec. 15; 261(35):16410–16413.

(List continued on next page.)

*Primary Examiner*—Louise N. Leary
(74) *Attorney, Agent, or Firm*—Townsend and Townsend and Crew (57) ABSTRACT

Methods for treating and preventing the onset and maintainance of multiple drug resistance (MDR) in animals undergoing chemotherapy for cancer are provided. According to the methods, target cells are depleted of adenosine 5'-monophosphate (AMP) and adenosine 5'-triphosphate (ATP) such that the cells are unable to support P-glycoprotein activity. According to one method, a population of target cells is obtained from a host and assayed for loss of methylthioadenosine phosphorylase (MTAse) activity. MTAse catabolizes methylthioadenosine to adenine for endogenous salvage incorporation into the intracellular AMP pool. MTAse deficient cells are treated with a purine synthesis inhibitor, such as L-alanosine, which starves the cells of adenine and suppresses P-glycoprotein activity. MTAse competent cells are also treated for MDR with purine synthesis inhibitors. In conjunction with treatment according to the invention, MTAse competent and deficient cells are also treated for malignancy with other anti-cancer drugs. A method for protecting non-malignant cells from adenine starvation during treatment of malignant cells according to the invention is provided.

12 Claims, 7 Drawing Sheets

OTHER PUBLICATIONS

Chen, Z.H., et al., "Gene deletion chemoselectivity: codeletion of the genes for p16(INK4), methylthioadenosine phosphorylase, and the alpha– and beta– interferons in human pancreatic cell carcinoma lines and its implications for chemotherapy," *Cancer Research* (1996) Mar. 1; 56(5):1083–1090.

Ahmed, N., et al., "Biochemical effect of three different inhibitors of purine/pyrimidine metabolishm on differentiation in HL60 cells," *Leuk. Res.* (1995) Apr.; (19)4:263–273.

Saverese, T.M., et al., "5'–deosy–5'–methylthioadenosine phosphorylase—V. Acycloadenosine derivatives as inhibitors of the enzyme," *Biochem. Pharmacol.* (1990) Dec. 1; 40(11):2465–2471.

Natsumeda, Y. et al., "Significance of purine salvage in circumventing the action of antimetabolites in rat hepatoma cells," *Cancer Res.* (1989) Jan. 1; 49(1):88–92.

Cristalli, G., et al., "Adenosine deaminase inhibitors. Synthesis and biological activity of deaza analogues of erythro–9–(2–hydroxy–3–nonyl) adenine," *J. Med. Chem.* 1988 Feb.; 31(2):390–393.

Thuillier, L., et al., "Consequences of the salvage of purine compounds on the proliferation of rat T–Lymphocytes with normal or inhibited purine de novo synthesis," *Biochim. Biophys. Acta* (1984) Apr. 24; 798(3):343–349.

Fukui, M., et al., New antitumor imidazole derivative, 5–carbamoyl–1 H–imidazol–4–yl piperonylate, as an inhibitor of purine synthesis and its activation by adenine phosphoriboxyltransferase, *Cancer Res.* (1982) Mar.; 42(3):1098–1102.

Jayaram, H. et al., "Analogs of L–aspartic acid in chemotherapy for cancer." *Cancer Trat Rep* 1979 Jun.; 63(6):1095–1108.

Wang, B., et al., "The effect of GP683, and adenosine kinase inhibitor, on the desflurane anesthetic requirement in dogs," *Anesth. Analg.* (1997) Sep.; 85(3):675–680.

Gilmour, J., et al., "Isolation, cloning and characterization of a low–molecular–mass purine nucleoside– and nucleotide–binding protein," *Biochem J.* (1997) Sep. 1; 326(Pt2):471–477.

Jiang, N., "Adenosine kinase inhibition protects brain against transient focal ischemia in rats," *Eur J. Pharmacol* (1997) Feb. 12; 320(2–3):131–137.

Golembiowska, K., et al., "Adenosine kinase inhibitors augment release of adenosine from spinal cord slices," *Eur J. Pharmacol* (1966) Jun. 27; 307(2):157–162.

Willis et al; Adv. Exp. Med. Biol.; vol. 122B, p 237–241; 1980.*

Guicherit et al; J. Biol. Chem; vol. 269, No. 6, p 4488–4496, 1994.*

* cited by examiner

```
   1  CCTGGTCTCG CACTGCTCAC TCCCGCGCAG TGAGGTTGGC ACAGCCACCG
  51  CTCTGTGGCT CGCTTGGTTC CCTTAGTCCC GAGCGCTCGC CCACTGCAGA
 101  TTCCTTTCCC GTGCAGACAT GGCCTCTGGC ACCACCACTA CCGCCGTGAA
 151  GGTGAGATGA GCCCTCCCAG CCGCAGCGGT TCGCCTGCCG GATGCCTTCN
 201  NNNNNNNNNN NNNNNNNNNN NNNNNNNNNN NNNNNNNNNN NNNNNNNNNN
 251   CCTTCAAATG TTTGTTGATT TTTATGGAAG GCTTTGAAAT ATTTGTTGAT
 301  TGATGTTCAG TAATTTTCAG ATTTCAAAAA AATAACTAGG GCTTGGCAGG
 351  AATGGAGAAG AGCATATGAA TAAATGAATT TGCTTAGAAT CTTATTTCTA
 401   ATAAAAATTA CCAAATACAA TAATCTTATA TGTCTTTTTC TGCTCTTAGA
 451  TTGGAATAAT TGGTGGAACA GGCCTGGATG ATCCAGAAAT TTTAGAAGGA
 501  AGAACTGAAA AATATGTGGA TACTCCATTT GGCAAGGTTA ATATCCAACT
 551  TGTGGAGACA TGTTTTNNNN NNNNNNNNNN NNNNNNNNNN NNNNNNNNNN
 601  TTCTCTAAGT TGTATCCTCA GACTCTTCAG ATTCCATGAG TCCTGTTGTG
 651  GTTGAACAAT TATAATTTAC ATACCTGTTT TTTAAATCAC TGAGTTAAAT
 701  GTCATTTTTT TCATTGCATG CAGCCATCTG ATGCCTTAAT TTTGGGGAAG
 751  ATAAAAAATG TTGATTGCGT CCTCCTTGCA AGGTATGGTA NNNNNNNNNN
 801  NNNNNNNNNN NNNNNNNNNN NNNNNNNNNN NNNNNNNNNN NNNNNNNNNN
 851  AAGCTTGATA CTCATCACGG GTTAACAATT TCTTCTCTCC TTCCATAGGC
 901  ATGGAAGGCA GCACACCATC ATGCCTTCAA AGGTCAACTA CCAGGCGAAC
 951  ATCTGGGCTT TGAAGGAAGA GGGCTGTACA CATGTCATAG TGACCACAGC
1001  TTGTGGCTCC TTGAGGGAGG AGATTCAGCC CGGCGATATT GTCATTATTG
1051  ATCAGTTCAT TGACAGGTAA GCAGTCATAC AAAATGCTTT AGGCTATTGT
1101  AGCTGGTCAT TTTCAGCTCA AATGGACGAC NNNNNNNNNN NNNNNNNNNN
1151  NNNNNNNNNN NNNNNNNNNN NNNNNNNNNN NNNNNNNNNN NNNNNNNNNN
1201  GAGGTCGACG GTATCGATAA GCTTTGTAAA CAATTGTCTT TAGCTTATCC
1251  AGAGGAATTG AGTCTGGAGT AAAGACCCAA ATATTGACCT AGATAAAGTT
1301  GACTCACCAG CCCTCGGAGG ATGGAAAGAT GGCCTTAAAA TAAAACAAAC
1351  AAAAACCTTT TTTGCTTTAT TTGTAGGAC CACTATGAGA CCTCAGTCCT
```

*FIG. 4A.*

1401 TCTATGATGG AAGTCATTCT TGTGCCAGAG GAGTGTGCCA TATTCCAATG
1451 GCTGAGCCGT TTTGCCCCAA AACGAGAGAG GTGTGTAGTC TTTCTGGAAG
1501 GTGTACCAGA ATAAATCATG TGGGCTTGGG GTGGCATCTG GCATTTGGTT
1551 AATTGGCAGA CGGAGTGGCC CCATACCCTC ACTCAAGTTT GCTTTGTATT
1601 ATGCAAGTTT ATGGAGAGTT ATTTCCTGTT GCTAATAATT TNNNNNNNNN
1651 NNNNNNNNNN NNNNNNNNNN NNNNNNNNNN NNNNNNNNNN NNNNNNNNNN
1701 AAGTGCAGCC TTAAGTTGTG CATGTGCTAG TATGTTTTGA AGTTTCTGGT
1751 TTTTCTTTTC TAGGTTCTTA TAGAGACTGC TAAGAAGCTA GGACTCCGGT
1801 GCCACTCAAA GGGGACAATG GTCACAATCG AGGGACCTCG TTTTAGCTCC
1851 CGGGCAGAAA GCTTCATGTT CCGCACCTGG GGGGCGGATG TTATCAACAT
1901 GACCACAGTT CCAGAGGTGG TTCTTGCTAA GGAGGCTGGA ATTTGTTACG
1951 CAAGTATCGC CATGGGCACA GATTATGACT GCTGGAAGGA GCACGAGGAA
2001 GCAGTAGGTG GAATTCTTTT CTAAGCACAT ATAGCATGGG TTTCTGGGTG
2051 CCAATAGGGT GTCTTAACTG TTTGTTTCTA TTACGTTAGT TTCAGAAAGT
2101 GCCTTTCTAC AAGGTTTTGA AGTTGTTAAT ATTTCTGTA GTTCCATTGG
2151 AAGGTAAGAA CAAAGATCAA AAGAAAGAAA GAGACACTTT TACCCAAGGA
2201 TCAGTAGTGA AAATAGTACA TTGTAGGCAT GTAGATGTGT TGAGAATCAT
2251 ACTAAGACTT GGGCCTTNNN NNNNNNNNNN NNNNNNNNNN NNNNNNNNNN
2301 NNNNNNNNNN NNNNNNNNNN NNNNNNNNNN NNNNNNNNNN NNNNNNNNNN
2351 GAGCTCCGAA AAATGTTTTA TGACTAGCAG TGGAATTTTA AGTTCTAGTA
2401 ACCTCCAGTG CTATTGTTTC TCTAGGTTTC GGTGGACCGG GTCTTAAAGA
2451 CCCTGAAAGA AAACGCTAAT AAAGCCAAAA GCTTACTGCT CACTACCATA
2501 CCTCAGATAG GGTCCACAGA ATGGTCAGAA ACCCTCCATA ACCTGAAGGT
2551 AAGTGTCAGC CATGGACAAC CAGGCATGTC TGGAGACTCT CTATTGTCTT
2601 CTCCTCTCAC TAGCATCACA CCCGGGGGTC CTCATGTATT TTATGCCAGC
2651 CTANNNNNNN NNNNNNNNNN NNNNNNNNNN NNNNNNNNNN NNNNNNNNNN
2701 CTGTAGAATT TATTTAAAGT GTATGTTTCC TGCGTCCTCA CTTTGATCTA
2751 GAAAATCAAA ATCTGGTTTT TTTTTTAACA AACATCTCAG TAATTACGCC
2801 AACATGTGAA TATCACTGCC TCCTTTCTTC CTTTCAGAAT ATGGCCCAGT

*FIG. 4B.*

```
2851  TTTCTGTTTT ATTACCAAGA CATTAAAGTA GCATGGCTGC CCAGGAGAAA
2901  AGAAGACATT CTAATTCCAG TCATTTGGGA ATTCCTGCTT AACTTGAAAA
2951  AAATATGGGA AAGACATGCA GCTTTCATGC CCTTGCCTAT CAAAGAGTAT
3001  GTTGTAAGAA AGACAAGACA TTTGTGTGTA TTAGAGACTC CTGAATGATT
3051  TAGACAACTT CAAAATACAG AAGAAAAGCA AAA
```

METHOD FOR SUPPRESSING MULTIPLE DRUG RESISTANCE IN CANCER CELLS

CROSS REFERENCE TO RELATED U.S. APPLICATIONS

This is a continuation-in-part of U.S. patent application Ser. No. 08/612,542, filed Mar. 8, 1996 now U.S. Pat. No. 5,840,505; which is in turn a continuation-in-part of U.S. patent application Ser. No. 08/176,855, filed Dec. 29, 1993 now abandoned.

STATEMENT REGARDING FEDERALLY FUNDED RESEARCH

The work described in this application was supported by finding from the National Institutes of Health under Grant No. GM23200. The government may have certain rights to the invention.

FIELD OF THE INVENTION

The invention relates to pharmaceutical agents and methods for use in the treatment of cancer. More specifically, the invention relates to treatment of cancer cells with L-alanosine to inhibit de novo adenosine 5'-triphosphate (ATP) synthesis in such cancer cells. In particular, the invention deprives cancer cells that have developed P-glycoprotein-mediated multiple drug resistance of the energy required to maintain such drug resistance.

HISTORY OF THE INVENTION

One of the greatest limitations on the efficacy of cancer chemotherapy is the tendency of cancer cells to develop broad-spectrum resistance to a host of anti-cancer and cytotoxic drugs. Such multiple drug resistance (MDR) is believed to occur to varying degrees in most cancers, either from the onset of the cancer or on recurrence following chemotherapy.

MDR is believed to be mediated by the activity of a cell surface phospho-glycoprotein, P-glycoprotein. Increased expression of the gene which encodes P-glycoprotein (mdr) is found in many malignant cells and may be upregulated by the onset of a malignancy and/or cellular contact with chemotherapeutic agetns. Once active, P-glycoprotein is believed to function as a "hydrophobic vacuum cleaner" which expels hydrophobic drugs from targeted cells. Such drugs include a host of anti-cancer drugs and cytotoxic agents, such as the Vinca alkaloids (e.g., vinblastine), the anthracyclines (e.g., doxorubicin), the epipodophyllotoxins (e.g., etoposide), the taxanes (e.g., taxol), antibiotics (e.g., actinomycin D), antimicrotubule drugs (e.g., colchicine), protein synthesis inhibitors (e.g., puromycin), toxic peptides (e.g., valinomycin), topoisomerase inhibitors (e.g., topotecan), DNA intercalators (e.g., ethidium bromide) and anti-mitotics.

MDR has been the subject of intense research for many years. Efforts to counter MDR have primarily involved the use of hydrophobic competitors for P-glycoprotein binding, such as calcium channel blockers, cephalosporins, steriods, immunosuppressants, antihypertensives, anti-arrhythmics, lipophilic cations, detergents and antidepressants. To varying degrees, most of these competitors eventually fail to sufficiently overcome MDR for reasons including their interference with chemotherapeutic drug uptake and unexpected toxicities.

The precise mechanism of MDR action for P-glycoprotein is not yet certain. However, it is clear that P-glycoprotein requires greatly increased stores of ATP (as compared to normal cells) to function. Thus, as mdr expression and P-glycoprotein activity increases in growing and/or metastasizing cancer cells, so too does synthesis and metabolic turnover of ATP by those cells. In order for cells to produce ATP, they must maintain a source of adenine, the metabolic substrate for synthesis of ATP. Failing an adequate natural source of adenine, cells can resort to an alternative pathway in which adenine is salvaged from metabolism of methylthioadenosine (MTA). Thus, de novo and salvage adenine metabolism is significantly increased in cells with active P-glycoprotein.

SUMMARY OF THE INVENTION

It has been discovered that MDR can be prevented or overcome in certain cancer cells by application of an inhibitor of de novo adenine synthesis to such cells. Cancer cells which are sensitive to the treatment of the invention are those which cannot salvage adenine by metabolism of MTA. In particular, cells from which the gene which encodes MTAse protein has been deleted are not able to metabolize MTA to adenine ("MTAse deficient cells"). In the presence of therapeutically effective dosages of a de novo AMP synthesis inhibitor, such cells become starved of adenine and cannot produce sufficient levels of ATP to maintain P-glycoprotein activity.

The invention provides a method for treating and preventing MDR in MTAse deficient cancers by contacting MTAse deficient cells with a therapeutically effective amount of a de novo purine synthesis inhibitor which inhibits de novo adenine synthesis. In one aspect of the inventive method, the purine synthesis inhibitor is L-alanosine.

A method is also provided for treating and limiting MDR in MTAse competent cancer cells. According to this aspect of the invention, MTAse competent cancers are treated with a combination of chemotherapeutic agents and purine synthesis inhibitors, thus limiting the acquisition and maintainance of MDR in such cells.

In another aspect, the invention provides a method for determining whether particular cancer cells are MTAse deficient (and therefore susceptible to treatment to prevent MDR) by providing assays to determine whether the cells lack MTAse protein. The preferred assay for use in this regard is one for detection of homozygous deletions from cells of the gene which encodes MTAse protein.

Also provided are kits for use in the methods of the invention which include reagents for use in performing the MTAse deficiency assay of the invention as well as pharmaceutical compositions of a purine synthesis inhibitor. In one aspect, the inhibitors provided are L-alanosine and/or its active metabolite, L-alanosinyl AICOR.

BRIEF DESCRIPTION OF THE DRAWINGS

FIGS. 2 and 3 (A–B) are graphs depicting the effect of administering various exogenous MTAse substrates to MTAse competent or MTAse deficient cell lines after treatment with L-alanosine.

DETAILED DESCRIPTION OF THE INVENTION

Effect of Purine Synthesis Inhibition on MDR

Based on early in vitro studies, the L isomer of a bacterial antibiotic alanosine (obtained from *Streptomyces alanosinicus;* hereafter, "L-alanosine"), appeared to have promise for use as an anti-viral and anti-tumor agent. In particular, it is believed that L-alanosine inhibits adenylosuccinate synthetase (ASS) conversion of inosine 5'-monophosphate (IMP) to AMP, thus depleting target cells of AMP and ATP (in the absence of adenine). However, clinical studies of the therapeutic efficacy of L-alanosine in human cancer patients have been disappointing (see, e.g., data collected in Tyagi and Cooney, *Adv. Pharmacol. Chemotherapy,* 20:69–120, 1984 [results then to date offered "little encouragement" regarding L-alanosine's efficacy for treatment of human cancers]; Creagan, et al, *Cancer,* 52:615–618, 1993 [Phase II studies had overall response rate of only 4%]; Creagan, et al., *Am.J.Clin.Oncol.,* 7:543–544, 1984 [Phase II study in melanoma patients; little therapeutic response observed]; VonHoff, et al., *Invest. New Drugs,* 9:87–88, 1991 [no objective responses observed in breast cancer patients]). Eventually, all clinical trials of L-alanosine for use in treatment of cancer were abandoned.

As described in co-pending, commonly owned U.S. patent application Ser. No. 08/612,542 (the disclosure of which is incorporated herein by this reference as though set forth here in full), it was discovered by the inventors that, while L-alanosine is not therapeutically effective against all cancer cells, it is therapeutically effective against MTAse deficient cells. Although not limited by any particular theory with respect to mechanism of action, it is believed that the efficacy of L-alanosine in treatment of MTAse deficient cancer cells is owing to its elimination of de novo adenine synthesis. Because MTAse deficient cells cannot salvage adenine through salvage pathways, the treated cells become starved of adenine (and, consequently, of ATP) and die.

More specifically, the activity of inhibitors of de novo purine synthesis (such as L-alanosine, methotrexate, 6-mercaptopurine, 6-thioguanine and dideazatetrahydrofolate) has been circumvented in vivo by salvage of hypoxanthine, which is abundant in plasma, for use as a substrate for AMP and ATP production. Hence, to date the in vivo performance of agents which block the adenine metabolic pathway for intracellular AMP and ATP production has been frustratingly poor.

However, with the development of an assay of sufficient sensitivity to identify homozygous deletions of the gene encoding MTAse in certain human cancer cells (see, commonly assigned U.S. patent application Ser. No. 08/827,342, filed Mar. 26, 1997, the disclosure of which is incorporated herein), it now appears that the tumors treated in the clinical trials of L-alanosine produced MTAse and were therefore able to provide sufficient adenine to maintain a pool of AMP despite inhibition of AMP production from IMP.

Although the present invention is similarly not to be limited by theories as to mechanism of action, it is believed that adenine starvation also deprives sensitive cells of sufficient ATP to maintain the P-glycoprotein activity essential to MDR.

Figure 6:
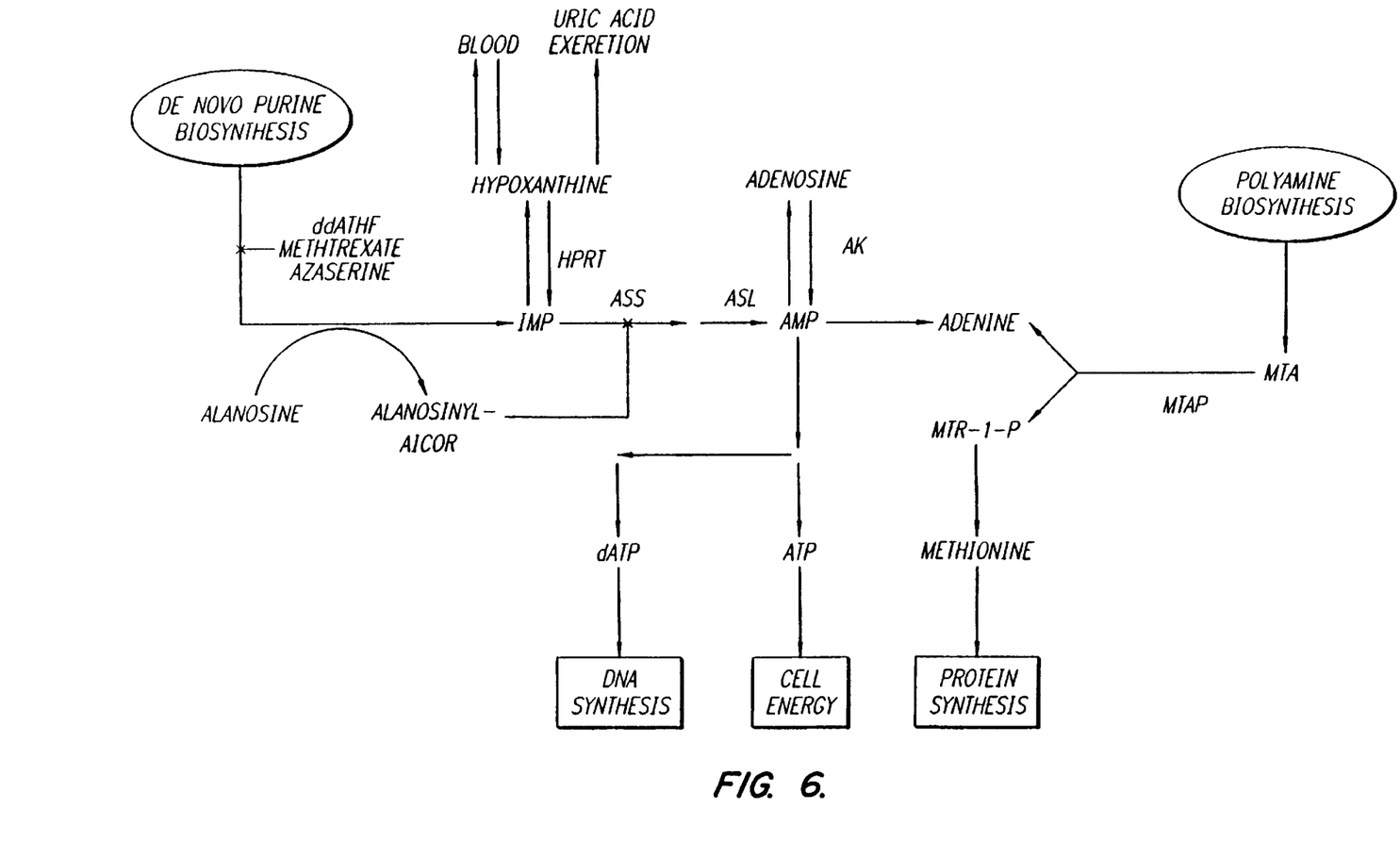
FIG. 6 is a chart depicting adenine metabolism in mammals.

To assist in understanding the invention, a chart depicting the intracellular metabolic pathways by which ATP is produced is provided in FIG. 6. In summary, there are three principal sources of substrates for intracellular ATP production. The first is catabolism of methylthioadenosine to adenine by MTAse. This pathway is blocked in MTAse deficient cells.

The second is conversion of IMP to AMP as an intermediate in ATP production by the activity of ASS or adenylsuccinate lyase (ASL). There are presently no known inhibitors of ASL activity. However, with loss of ASS activity (inhibited by L-alanosine), IMP→AMP conversion is substantially eliminated.

The third is hypoxanthine salvage to AMP. However, because IMP→AMP conversion occurs distal to hypoxanthine salvage, inhibition of ASS catabolism of IMP→AMP blocks the hypoxanthine salvage pathway.

Methods for Treatment and Prevention of MDR in MTAse-Deficient and MTAse-Competent Cancer Cells A. Pharmacology and Toxicity Parameters for L-alanosine Mammalian hosts who (a) are suffering from cancers determined to be MTAse deficient according to the MTAse deficiency assay of the invention (described in commonly owned U.S. Pat. No. 5,571,510 in and in co-pending, commonly owned U.S. patent application Ser. No. 08/827,342 and summarized below); and (b) are, or will be, undergoing treatment for the cancer with a drug whose effectiveness is known to decline in MDR cells, are treated with therapeutically effective dosages of a purine (adenine) synthesis inhibitor such as L-alanosine, L-alanosinyl-AICOR or hadacidin, preferably the former.

In such patients, the purine synthesis inhibitor plays a dual role; i.e., it suppresses MDR and acts as an anti-cancer agent by starving treated cells of adenine. Further treatment with additional anti-cancer therapies is acceptable, but not required. However, adenosine kinase inhibitors, such as those described below, can be expected to potentiate the activity of L-alanosine such that their use in conjunction with L-alanosine may be clinically desirable.

Mammalian hosts who (a) are suffering from MTAse competent cancers; and (b) are, or will be, undergoing treatment for the cancer with a drug whose effectiveness is known to decline in MDR cells, are treated with therapeutically effective dosages of a purine synthesis inhibitor and the therapeutic drug. The latter may include, but is not limited to, the Vinca alkaloids (e.g., vinblastine), the anthracyclines (e.g., doxorubicin), the epipodophyllotoxins (e.g., etoposide), the taxanes (e.g., taxol), antibiotics (e.g., actinomycin D), antimicrotubule drugs (e.g., colchicine), protein synthesis inhibitors (e.g., puromycin), toxic peptides (e.g., valinomycin), topoisomerase inhibitors (e.g., topotecan), DNA intercalators (e.g., ethidium bromide) and anti-mitotics.

In such patients, the principal role played by the purine synthesis inhibitor is as a MDR suppressor. Based on the poor outcome of clinical trials and usage of purine synthesis inhibitors as anti-cancer agents in MTAse competent cells, it is unlikely that the inhibitors will exert a significant anti-cancer effect on such cells. Rather, in this embodiment of the invention, the anti-cancer therapy is provided by other therapeutic agents.

Clinical trials and usage of purine synthesis inhibitors as chemotherapeutic agents, while generally unsuccessful, provide information to those of ordinary skill in the art concerning dosing and toxicity parameters for such inhibitors. In primates, approximately 75% of L-alanosine is excreted in urine in about 24 hours, primarily as the nucleoside forms of L-alanosinyl-IMP and L-alanosinyl-AICOR. Clearance from plasma after intravenous administration in humans is biphasic, with $t_{1/2}\alpha=14$ minutes and $t_{1/2}\beta=99$ minutes (where "$t_{1/2}$" is the half-life and times (t) are approximate).

In prior clinical trials, toxicity has been dose-limiting, including renal toxicity, stomatitis, esophagitis and, with lesser frequency, myelosuppression, headache, nausea and hypo- or hypertension. Renal toxicity occurred with single bolus dosing above 4 g/m² body weight. Further, two pediatric patients who received higher doses of about 350 mg/m² body weight per day in separate doses suffered liver failure. Stomatitis and esophagitis occurred after multiple bolus dosing. The other observed reactions were patient specific.

One phase II trial utilized continuous infusion at a dose of about 125 mg/m² body weight for 5 days in adults suffering from acute non-lymphoblastic leukemia. The dose limiting toxicity was mucositis.

It is predictable, however, that doses at far less than toxic levels will be useful in the methods of the invention. In MTAse deficient cancer cells, the lack of MDR and susceptibility of the cells to adenine starvation in the presence of an inhibitor of de novo purine synthesis provides the cells with sensitivity to treatment with such inhibitors. Thus, the high dosages required to overwhelm MTAse competent and drug resistant cells in prior clinical trials will not be required in the methods of the invention, which are specifically targeted to (a) MTAse deficient cells (which are uniquely susceptible to purine synthesis inhibitor treatment), or (b) MTAse competent cells which simultaneously undergo chemotherapy with drugs other than purine synthesis inhibitors.

Given the specificity of the methods of the invention, appropriate dosage ranges for treatment of mammals with a purine synthesis inhibitor such as L-alanosine will be about 50 mg/m² to 4 g/m², most often about 90 mg/m² to 125 mg/m² or a dosage sufficient to achieve about 1000–2000 nM concentration in blood within 24 hours of administration. For treatment of MTAse deficient cells, dosages at the lower end of the dosage range will be sufficient in most cases while dosages for MTAse competent cells may be increased, taking into account the total drug burden being placed on the host through concomittant administration of other chemotherapeutic agents in the latter instance. The chemotherapeutic agents applied in treatment of MDR in MTAse deficient cancers are provided in medically acceptable dosages, which are known to those of ordinary skill in the oncology field.

Preferably, non-malignant, MTAse competent cells are protected from any effect of exposure to purine synthesis inhibitors through administration of MTA or a suitable substrate analogue for use in adenine synthesis. Suitable compounds for use in this regard include MTA, 2'-5' dideoxyadenosine, 5'-deoxyadenosine, 2'-deoxy-5-deoxy-5'methylthioadenosine (see, e.g., Example III). It will be appreciated, however, that MTAse competent cells are capable of producing adenine from metabolism of methylthioadenosine for replenishment of the AMP cellular pool and therefore would not be expected to be depleted of AMP/ATP to the same extent as MTAse deficient cells.

In general, daily administration or continuous infusion of purine synthesis inhibitors at dosages less than those known to produce toxicities will be the preferred therapeutic protocol to enhance the anti-metabolite activity of the drugs. Any medically acceptable method of delivery and route of administration may be utilized, including intravenous, intraperitoneal, intranasal routes and direct introduction into tumor cells.

A pharmaceutical composition useful in the invention may include, or be administered during a course of treatment with, an adenosine kinase inhibitor. Suitable inhibitors include those having the formula:

(1)

wherein

Y is CH or N;

$R_1$ is H or an alkyl having from 1 to 18 carbon atoms;

$R_2$ is an O-aroyl having from 1 to 24 carbon atoms, $N_3$, $NH_2$, $NHNH_2$, $NHOH$, $OSO_2NH_2$, $NHOR_3$, SH, $SR_5$, $OR_4$, $NHR_6$ or halogen;

$R_3$ is an O-alkyl having from 1 to 18 carbon atoms or an O-aryl having from 6 to 24 carbon atoms;

$R_4$ is an alkyl having from 1 to 18 carbon atoms or CN;

$R_5$ is an alkyl having from 1 to 18 carbon atoms or CN;

$R_6$ is the same as $R_3$, $COR_3$, an acyloxymethyl having from 2 to 24 carbon atoms or $CONH_2$;

$R_7$ is OH, an O-aroyl having from 6 to 24 carbon atoms or an O-aryl having from 6 to 24 carbon atoms;

$R_8$ is OH, an O-aroyl having from 6 to 24 carbon atoms or an O-aryl having from 6 to 24 carbon atoms; and, $R_9$ is Cl, Br, I or an alkyl having from 1 to 18 carbon atoms, or halogenated derivatives or a salt thereof.

Or, alternatively, an adenosine kinase inhibitor having the formula:

(2)

wherein

R$_2$ is H, OH, an O-aroyl having from 1 to 24 carbon atoms, $_2$NH, NH$_2$NH, NHOH, OSO$_2$NH$_2$, NHOR$_3$, SH, SR$_5$, OR$_4$, NHR$_6$ or halogen, wherein R$_3$ is an O-alkyl having from 1 to 18 carbon atoms or an O-aryl having from 6 to 24 carbon atoms; R$_4$ is an alkyl having from 1 to 18 carbon atoms or CN; R$_5$ is an alkyl having from 1 to 18 carbon atoms or CN; and, R$_6$ is the same as R$_3$, COR$_3$, an acyloxymethyl having from 2 to 24 carbon atoms or CONH$_2$;

R$_7$ is an O-aroyl having from 6 to 24 carbond atoms, an O-aryl having from 6 to 24 carbon atoms, hydroxyl or SO$_3$;

R$_8$ is an O-aroyl having from 6 to 24 carbond atoms, an O-aryl having from 6 to 24 carbon atoms, hydroxyl or SO$_3$; provided that when R$_7$ is SO$_3$, so is R$_8$; and, R$_{10}$ is an O-alkyl having from 1 to 18 carbon atoms, an O-acyl having from 1 to 18 carbon atoms, halogen, o-tosyl or OSO$_2$R$_{11}$, wherein further R$_{11}$ is an alkyl having from 1 to 18 carbon atoms or an aryl having from 6 to 24 carbon atoms, or halogenated derivatives or a salt thereof.

The range of potency of the adenosine kinase inhibitors described above is: hydroxyl>amino≧deoxy>fluoro>chloro >azido. For example, Ki values for the 5'-hydroxyl and 5'-amino variants of the above-described compounds are 80 nM and 150 nM, respectively. These compounds are, respectively, 15-fold and 75-fold less toxic than 5-iodotubercin, a known adenosine kinase inhibitor. In mice, oral dosages of 30 mg/kcg of 5'-hydroxyl variants were effective in inhibiting inflammation in pleurisy model (Cottam, et al., *J.Med.Chem.,* 36:3424–2430 (1993; incorporated herein for reference); those of ordinary skill in the art will be able to readily calculate a dosage concentration to produce equivalent anti-inflammatory activity in other mammalian species, increasing dosages as required by the presenting condition of the patient, potency of the administered compound and method of drug delivery employed.

Those of ordinary skill in the art will know of, or will be able to readily ascertain the identity of, other adenosine kinase inhibitors useful in the invention, such as 5-iodotubercin, 5'-N-ethylcarboxamidoadenosine, 2-methyladenosine, N6-cyclohexyladenosine, N-6-L-phenylisopropyladenosine, 2-chloroadenosine and 6-methylmercaptopurine riboside, P1,P4-(di-adenosine5')-tetraphosphate and other 5'-hydroxyl adenosine analogs joined by phosphoryl bridges to a phosphoryl group acceptor (Cottam, et al., supra; Lin, et al., *Mol.Pharmacol.,* 34:501–505 (1988) and Bone, et al., *J.Biol.Chem.,* 261:6410–16413 (1986)).

Pharmaceutically acceptable carriers acceptable for use with drugs administered according to the invention include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. The drugs may also be provided in a targeted delivery system, such as a liposome. Preservatives and other additives may also be present such as, for example, antimicrobials, antioxidants, chelating agents, and inert gases and the like. A composition of drugs may also be lyophilized using means well known in the art, for subsequent reconstitution and use according to the invention.

Method for Determining Whether Tumor Cells are MTAse Deficient or MTAse Competent A. Polynucleotide Reagents for Use in Identifying MTAse Deficient Cells The preferred method for determining whether a particular population of cells are MTAse deficient is by hybridization assay to detect homozygous deletions of the gene which encodes MTAse from the cells. Screening procedures which rely on nucleic acid hybridization make it possible to detect any polynucleotide sequence (and, by inference, any protein encoded by such polynucleotide sequence) in any organism, provided the appropriate probe is available.

A complete description of hybridization techniques suitable for use in the invention, as well as a description of the gene which encodes MTAse, are set forth in co-pending, commonly assigned U.S. patent application Ser. No. 08/827, 342, the disclosure of which is incorporated herein by this reference together with any amendments which may be made thereto. For ease of reference, the polynucleotide sequence of the gene which encodes MTAse is described herein at SEQ.ID.No.1 in the appended Sequence Listing and in FIG. 4, where coding regions of the gene are identified by underlining.

Genomic MTAse polynucleotide is located on chromosome 9 at region p21. Interestingly, a very high percentage of cells which have a homozygous deletion of the gene which encodes tumor suppressor p16 also have a homozygous deletion of the gene which encodes MTAse. Thus, an alternative means of detecting homozygous deletions of the latter gene (for MTAse) is by detecting a homozygous deletion of the former gene (for p16). For further reference in this regard, see commonly assigned, co-pending U.S. patent application Ser. No. 08/227,800, the disclosure of which is incorporated herein by this reference.

A strain of *E. coli* containing the full-length genomic DNA for rat MTAse was deposited with the American Type Culture Collection, Rockville, Md. by mailing before Dec. 29, 1993 and accorded, collectively, Designation Nos. 55536, 55537, 55538, 55539 and 55540. No admission that this deposit is necessary to enable one to practice the invention is made or intended. The deposit will, however, be maintained in viable form for whatever period is or may be required by the patent laws applicable to this disclosure.

To determine whether the MTAse gene has been homozygously deleted from the cells of interest, an assayable sample of cells is obtained from the host. For example, the sample may comprise a body fluid or cells, e.g., from a host tissue or tumor. Such samples are obtained using methods known in the clinical art, e.g., tumor cells may be acquired by biopsy or surgical resection.

Preferably, the cells are essentially free from "contaminants"; i.e., cells, proteins and similar components which could falsify the result of the assay. For example, where solid tumors are the source for an assayable cell sample, normal non-malignant cells and the MTAse which may be released from normal cells during the procedure performed to obtain the biological sample would be considered to be contaminants. Such contaminants may be removed by conventional purification techniques; e.g., affinity chromatography with an anti-MTAse antibody.

Because the invention is directed toward detecting the presence or absence of this gene in a sample of cells which are suspected of being MTAse negative, nucleic acids in the sample will preferably be amplified to enhance the sensitivity of the detection method. This amplification is preferably accomplished through the use of the polymerase chain reaction (PCR), although the use of a chain reaction in the polymerization step is not absolutely necessary.

The nucleic acid to be amplified in the sample will consist of genomic or wild-type DNA that would normally be expected to encode MTAse if present in the sample (see, SEQ.ID.No.1). MTAse encoding DNA (hereafter the "target DNA") is believed to be present in all normal mammalian cells, including human cells.

For use as a control or as a source of oligonucleotide probes and primers, genomic MTAse-encoding DNA may be isolated according to methods known in the art such as the method described by Maniatis, et al. in *Molecular Cloning: A Laboratory Manual* (Cold Spring Harbor Laboratory, 1982). A working example demonstrating the isolation of a genomic clone of the human MTAse gene is provided herein wherein a cosmid gene library is screened using an MTAse cDNA oligonucleotide probe (see, Example III). However, those skilled in the art will recognize that other suitable means of obtaining MTAse encoding DNA can be used.

For example, a cDNA library believed to contain a polynucleotide of interest can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucleotide of interest. Alternatively, a cDNA library can be screened indirectly for expression of peptides of interest (e.g., MTAse protein) having at least one epitope using antibodies specific for the peptides. Such antibodies can be either polyclonally or monoclonally derived and used to detect expression product indicative of the presence of cDNA of interest (see, for further reference, Maniatis, et al., *Molecular Cloning: Laboratory Manual* (Cold Spring Harbor Lab., New York, 1982).

Polynucleotides for use as controls, probes or primers in the invention can also be synthesized using techniques and nucleic acid synthesis equipment which are well-known in the art. For reference in this regard, see Ausubel, et al., *Current Protocols in Molecular Biology,* Chs. 2 and 4 (Wiley Interscience, 1989).

B. Amplification of MTAse Encoding Genomic DNA and Hybridization Assay Therefor

To enhance the sensitivity of the hybridization assays of the invention, the cell sample to be assayed is preferably subjected to conditions favoring the selective amplification of the target nucleic acid. Preferably, the target nucleic acid will be a polynucleotide portion of the gene which encodes MTAse (i.e., the "target polynucleotide"). The preferred means of amplifying the target polynucleotide is by PCR.

PCR is an in vitro method for the enzymatic synthesis of specific DNA or RNA sequences using oligonucleotide primers that hybridize to specific nucleic acid sequences and flank the region of interest in target nucleic acid. A repetitive series of cycles of template denaturation, primer annealing and enzymatic extension of the annealed primers results in an exponential accumulation of a specific nucleic acid fragment defined at its termini by the 5' ends of the primers. The resulting products (PCR products) synthesized in one cycle act as templates for the next; consequently, the number of target nucleic acid copies approximately doubles in every cycle.

The basic PCR techniques are described in U.S. Pat. Nos. 4,683,195 and 4,683,202 to Mullis, et al., the disclosures of which are incorporated herein as examples of the conventional techniques for performance of the PCR. However, the invention is not intended to be limited to the use of the PCR techniques which are taught in the '202 patent to Mullis, et al. Since the development of the Mullis, et al technique, many PCR based assays have been developed which utilize modifications of that technique. These modifications are well-known in the art and will not, therefore, be described in detail here. However, for the purpose of illustrating the scope of the art in this field, several of these modifications are described as follows.

A PCR technique which provides an internal amplification standard using a competitor template which differs from the target nucleic acid in sequence and size is described in *Proc. Natl. Acad. Sci. USA* (1990) 87:2725–2729 (Gilliland, et al., authors). Another technique for performing "competitive" PCR which utilizes templates which differ in sequence but not in size is described in commonly owned U.S. Pat. No. 5,747,251, (issued from Ser. No. 08/442,141). This technique is a particularly preferred technique for its use of enzyme-linked immunoabsorbent assay (ELISA) technology to analyze the amplified nucleic acid(s). A noncompetitive PCR technique which utilizes site-specific oligonucleotides to detect mutations or polymorphisims in genes which may also be applied to the method of the invention is described in *Proc. Natl. Acad. Sci. USA* (1989) 86:6230–6234 (Saiki, et al., authors). Each of these techniques has the advantage of utilizing hybridization probes which assist in eliminating false positive results derived from any nonspecific amplification which may occur during the PCR. Each of these references is incorporated herein.

For further background, those skilled in the art may wish to refer to Innis, et al., "Optimization of PCR's", PCR Protocols: A Guide to Methods and Applications (Acad. Press, 1990). This publication summarizes techniques to influence the specificity, fidelity and yield of the desired PCR products.

Oligonucleotide primers (at least one primer pair) are selected which will specifically hybridize to a small stretch of base pairs on either side (i.e., 5' and 3') of the MTAse target polynucleotide (i.e., "flanking sequences"). Those skilled in the art will readily be able to select suitable primers without undue experimentation based on the polynucleotide sequence information set forth in the Sequence Listing appended hereto as SEQ. ID. No. 1 and in FIG. 4.

For primer design, it is important that the primers do not contain complementary bases such that they could hybridize with themselves. To eliminate amplification of any contaminating material which may be present in the sample, primers are preferably designed to span exons (which, for the MTAse gene, are underlined in FIG. 4).

As noted above, it may not be necessary to utilize the chain reaction in this polymerization step in order to adequately amplify the nucleic acids in the sample. For example, where the technique described in U.S. Pat. No.

5,747,251, supra is utilized so the polymerization step is performed on solid phase support means and is followed by hybridization with target polynucleotide specific probes, the sensitivity of the assay will be such that a single polymerization of the target polynucleotide may be all that is necessary.

Once the amplification step is complete, the PCR products are assayed to determine thereby whether the gene to encode MTAse is present in the sample. Preferably, the double-stranded PCR products will be bound to the solid phase so their strands may be separated by denaturation, thereby allowing sequence-specific probes to hybridize to the bound antisense strand of the PCR product to detect the gene substantially as described in Kohsaka, et al., supra. Alteratively, the PCR products will be removed from the reaction environment and separated from the amplification mixture prior to the addition of probes for hybridization to the double-stranded PCR products. In this latter approach, the PCR products are separated from the amplification mixture according to methods known in the art with regard to the particular method chosen for detection; e.g., by gel exclusion, electrophoresis or affinity chromatography.

Detection of the amplified product may be achieved by using hybridization probes which are stably associated with a detectable label. A label is a substance which can be covalently attached to or firmly associated with a nucleic acid probe which will result in the ability to detect the probe. For example, a level may be a radioisotope, an enzyme substrate or inhibitor, an enzyme, a radiopaque substance (including colloidal metals), a fluorescors, a chemiluminescent molecule, liposomes containing any of the above labels, or a specific binding pair member. A suitable label will not lose the quality responsible for detectability during amplification.

Those skilled in the diagnostic art will be familiar with suitable detectable labels for use in in vitro detection assays. For example, suitable radioisotopes for in vitro use include $^3H$, $^{125}I$, $^{131}I$, $^{32}P$, $^{14}C$, $^{35}S$. Amplified fragments labeled by means of a radioisotope may be detected directly by gamma counter or by densitometry of autoradiographs, by Southern blotting of the amplified fragments combined with densitometry. Examples of suitable chemiluminescent molecules are acridines or luminol. Target sequences hybridized with probes derivatized with acridium ester are protected from hydrolysis by intercalation. Examples of suitable fluorescers are fluorescein, phycobiliprotein, rare earth chelates, dansyl or rhodamine.

Examples of suitable enzyme substrates or inhibitors are compounds which will specifically bind to horseradish peroxidase, glucose oxidase, glucose-6-phosphate dehydrogenase, β-galactosidase, pyruvate kinase or alkaline phosphatase acetylcholinesterase. Examples of radiopaque substance are colloidal gold or magnetic particles.

A specific binding pair comprises two different molecules, wherein one of the molecules has an area on its surface or in a cavity which specifically binds to a particular spatial and polar organization of another molecule. The members of the specific binding pair are often referred to as a ligand and receptor or ligand and anti-ligand. For example, if the receptor is an antibody the ligand is the corresponding antigen. Other specific binding pairs include hormone-receptor pairs, enzyme substrate pairs, biotin-avidin pairs and glycoprotein-receptor pairs. Included are fragments and portions of specific binding pairs which retain binding specificity, such a fragments of immunoglobulins, including Fab fragments and the like. The antibodies can be either monoclonal or polyclonal. If a member of a specific binding pair is used as a label, the preferred separation procedure will involve affinity chromatography.

If no amplified product can be detected in the assay described above, this is indicative of MTAse deficiency in the cells present in the sample. Because normal (i.e., nonmalignant) cells will always be expected to have MTAse encoding gene present in detectable quantities (even with loss of one allele), a finding that cells lack an MTAse encoding gene (i.e., have a homozygous deletion of the gene) indicates that the cells assayed lack both catalytically active and catalytically inactive MTAse.

However, where desired, the sample can be prescreened for MTAse catalytic activity using the method described by Seidenfeld, et al., *Biochem. Biophys. Res. Commun.*, 95:1861–1866 (1980); see also, Example I, infra). The inventive assay will then be used to determine whether the gene encoding MTAse is present in cells in the sample. The sample may also be tested for the presence of catalytically active or inactive protein for the purpose of screening out cellular contaminants in the sample to be assayed; i.e., nonmalignant cells. A suitable immunoassay for alternative use in this regard (i.e., in lieu of the hybridization assay) is described in Nobori, et al., *Cancer Res.* 53:1098–1101 (1991) and in co-pending, commonly assigned U.S. patent application Ser. No. 08/827,342, the disclosure of which has been incorporated herein.

C. MTAse Deficient Cells

Using the assay techniques described above, the following human primary tumors have been determined to be MTAse deficient. It will be understood that this list is representative, but not exhaustive, of the cancer types which may be determined to be MTAse deficient using the assay methods described.

Acute lymphoblastic leukemias (approximately 80% occurrence)

Gliomas (approximately 67% occurrence)

Non-small cell lung cancers (approximately 18% occurrence)

Urothelial tumors (e.g., bladder cancer; incidence varies with tumor type)

Based on these data, MTAse deficiency should be strongly suspected of patients suffering from these conditions. Thus, cell samples from such patients should be routinely assayed for MTAse deficiency to determine whether the patient would be likely to benefit from the therapeutic method of the invention.

Cell samples from other cancer patients should be assayed for MTAse deficiency as clinically indicated. For reference, primary tumor samples from patients suffering from the following conditions have not been found to be MTAse deficient (i.e., the cancers are "MTAse competent"):

Breast cancer

Colon cancer

Head and Neck cancer

Melanoma

Renal cancer

Adult non-lymphoblastic leukemias

Certain acute leukemias (adult and juvenile)

Clinical trials have been conducted using L-alanosine to treat the above-listed MTAse competent cancers, with no appreciable success.

The invention having been fully described, its practice is illustrated by the examples set forth below. It will be understood, however, that the examples do not limit the scope of the invention, which is defined by the appended claims. Standard abbreviations are used throughout the Examples, such as "ml" for milliliter, "h" for hour and "mg" for milligram.

EXAMPLE I

Suppression of MDR in Resistant Cells

Figure 1A:
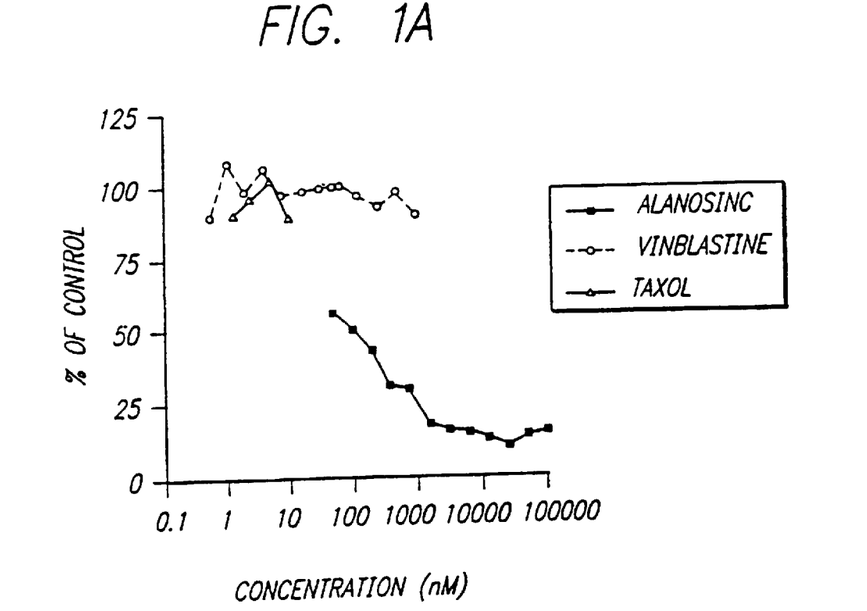
FIG. 1A is a graph depicting the effect of L-alanosine and different chemotherapeutic agents (vinblastine and taxol) on a MDR cancer cell line (MV522Q6).
Figure 1B:
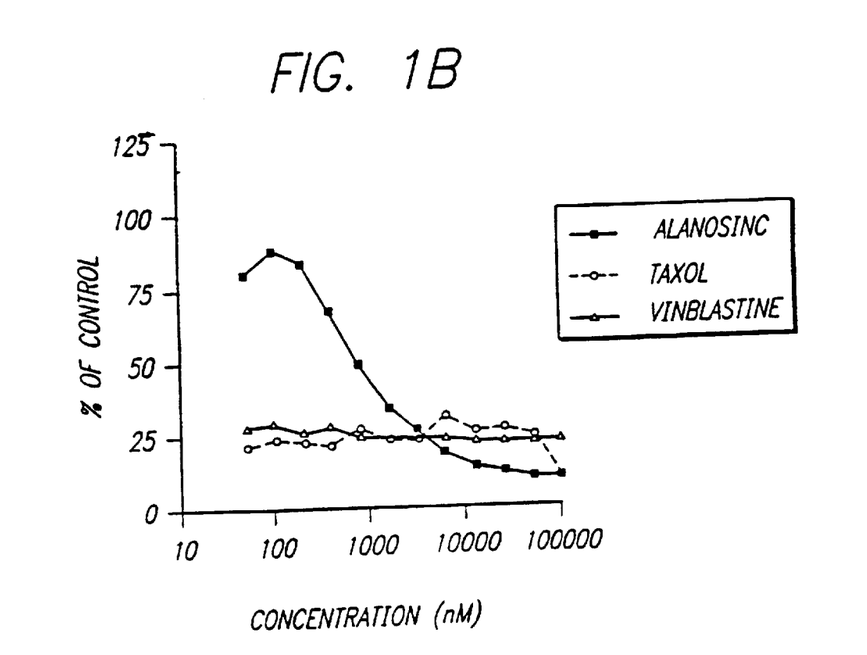
FIG. 1B is a graph depicting the effect of the same drugs on the cell line before acquisition of resistance W522). Comparing the two, the sensitivity of the resistant cell line to chemotherapy with vinblastine and taxol is greatly reduced. However, the adenine synthesis inhibitor L-alanosine is as, if not more, potent in the resistant cell line than in the non-resistant cell line.

MV522 is a human cancer cell line; MV522Q6 is a variant of the cell line with MDR. Each cell line was grown in a monolayer as and contacted with 10 μM of a chemotherapeutic agent and/or L-alanosine (as shown in FIGS. 1A and 1B). Growth, or the lack thereof, was measured in each population of cells by reduction of a tetrazolium dye after three days in culture.

FIG. 1A is a graph depicting the effect of L-alanosine and different chemotherapeutic agents (vinblastine and taxol) on a MDR cancer cell line (MV522Q6). FIG. 1B is a graph depicting the effect of the same drugs on the cell line before acquisition of resistance (MV522). Comparing the two, the sensitivity of the resistant cell line to chemotherapy with vinblastine and taxol is greatly reduced. However, the adenine synthesis inhibitor L-alanosine is nearly 10 times as potent in the resistant cell line than the other agents tested.

For further confirmation of these results, two additional cell lines were tested which are available from the American Type Culture Collection (ATCC), Rockville, Md., USA: ATCC CRL-1976; MES-SA and ATCC CRL-1977; MES-SA/Dx5. The latter is a drug resistant clone of the former cell line. The resistance levels exhibited by each cell line to conventional chemotherapeutic agents (e.g., vinblastine and taxol) is described in Chen, et al., *J.Biol. Chem.*, 272:5974–5982 (1997); generally, MES-SA/Dx5 is highly resistant to these agents, while MES-SA is not.

Consistent with the data obtained in the MV522/MV522Q6 cell lines, the MES-SA/Dx5 drug resistant cell line was significantly more affected by L-alanosine than by the other agents tested (data not shown).

EXAMPLE II

Protection of MTAse Competent Healthy Cells with MTAse Substrates

Figure 2:
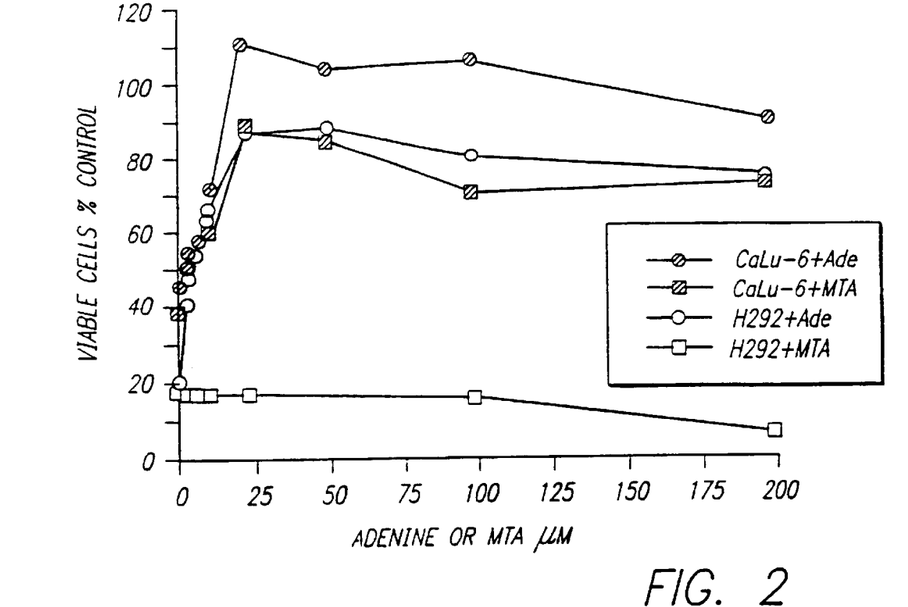

The selective inability of MTAse deficient NSCLC cells to proliferate in the presence of L-alanosine (at 40 μM) despite the addition to each culture of the MTAse substrate methylthioadenosine(MTA) was confirmed in a comparison of two cell lines, MTAse competent Calu-6 and MTAse deficient H292 (FIG. 2). Control cultures containing adenine (tAde) proliferate despite L-alanosine, confirming that the selective toxicity is due to a failure of MTAse-deficient cells to metabolize MTA to adenine.

Figure 3A:
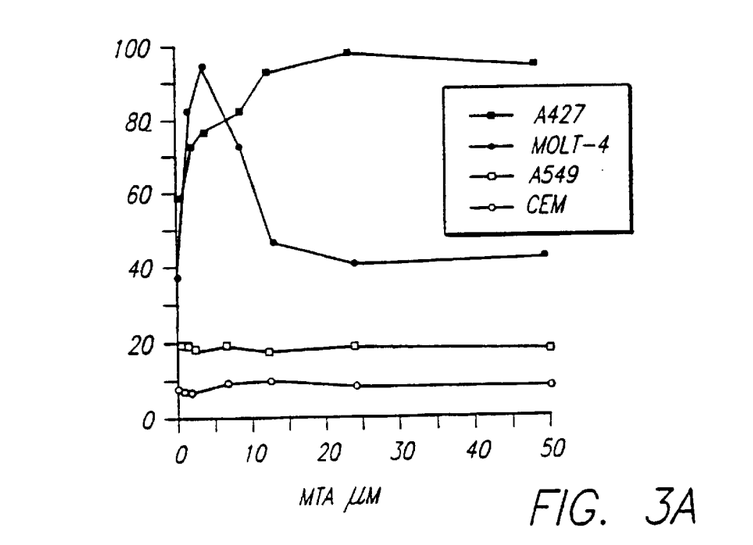
Figure 3B:
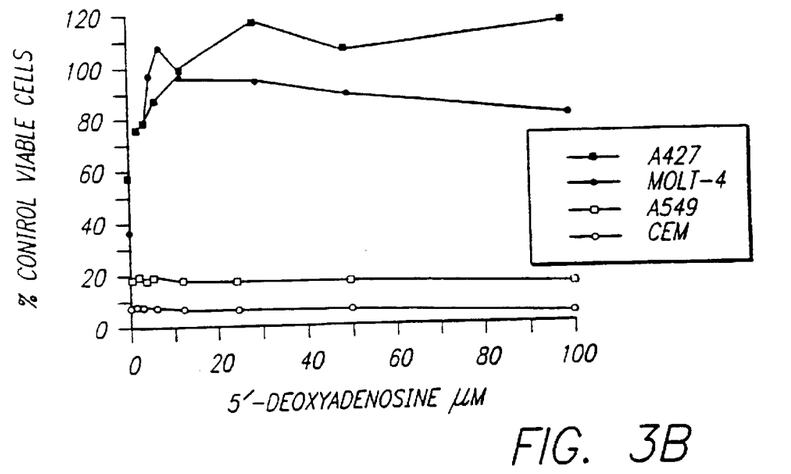

For further comparison, the addition of MTA or the MTA substrate analogue 5'-deoxyadenosine resulted in growth restoration only for MTAse competent A427 cells and MOLT-4 cells, whereas MTAse deficient A549 and CEM cells remained growth inhibited (FIGS. 3A and B). Because MTA is a feedback inhibitor of spermine synthetase, some cell lines such as MOLT-4 are inhibited by high concentrations. This results in a biphasic growth restoration curve with increasing MTA concentration (FIG. 3A).

EXAMPLE III

Cloning and Partial Characterization of the MTAse Genomic Clone

A genomic clone of human MTAse was isolated as follows. A cosmid gene library constructed from human placenta DNA (Clontech) was screened using MTAse cDNA gene probe, the Not I/EcoRi fragment from subclone MTAP-7. Transformed *E. coli* cells from the library are plated on LB plates containing ampicillin (50 mg/l) with a colony density of $1-2 \times 10^4/135 \times 15$ mm plate.

The following procedures were performed. From half a million colonies, a single positive colony designated as MTAP-10 was isolated and partially characterized by PCR analysis and by direct sequencing. Two primers, a sense oligonucleotide located 120 bp upstream of the stop codon and an anti-sense oligonucleotide located 20 bp downstream of the stop codon were synthesized and used for PCR analysis. PCR was performed for 25 cycles, each cycle consisting of denaturation (92° C., 1 min), annealing (55° C., 2 min) and extension (72° C., 5 min). The PCR products were separated on a 0.8% agarose gel.

Figure 4C:
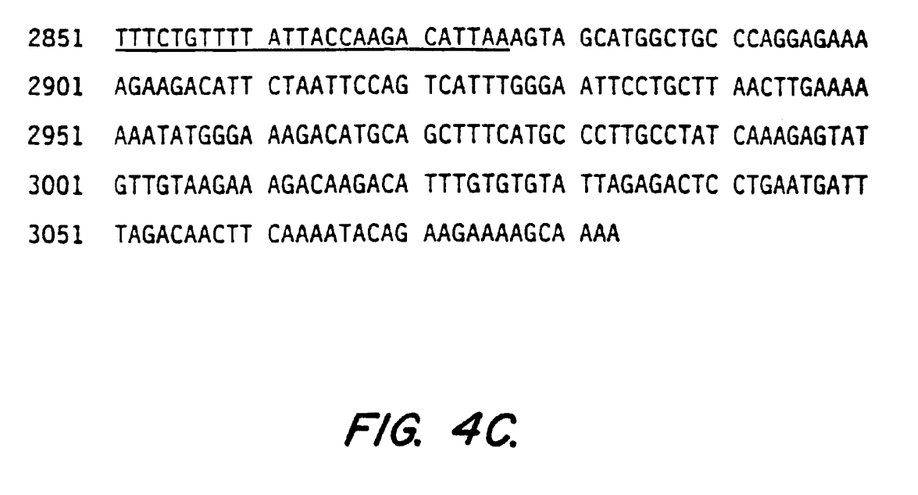
FIG. 4 is a nucleotide sequence for genomic MTAse (SEQ.ID.No.1) wherein the exons are underlined.

The location of exons identified to date in the MTAse gene using the above-described technique is depicted in FIG. 4 by underlining.

EXAMPLE IV

Application of MTAse Sequence-Specific Oligonucleotides to Malignant Cell Lines to Detect the Presence or Absence of MTAse Therein To test the usefulness of oligonucleotide probes developed from the MTAse genomic clone (SEQ.ID.No. 1) applied to several human lung cancer cell lines which were known to contain MTAse competent (Calu-6; ATCC Designation No. HTB-56) and deficient cells (A549; ATCC Designation No. CCL-185). Genomic DNA was isolated as described in Example III and 1 microgram thereof was used for PCR.

Amplification was performed for 40 cycles as described above, with each cycle consisting of denaturation (92° C., 1 min), annealing (55° C., 1 min), and extension (72° C., ½ min). The PCR products were analyzed on a 1.5% agarose gel. No MTAse was detected in cell lines which were known to be MTAse deficient, while MTAse was detected in the MTAse competent cell lines.

EXAMPLE V

L-Alanosine Inhibition of MTAP-Deficient Tumors after Daily Injection into Nude Mice with Established Tumor Xenografts $10^7$ A549 or A427 NSCLC cells were injected subcutaneously into 6-week old Balb/c athymic nude mice. When tumors had reached approximately 0.4 cm diameter, treatment was begun with L-alanosine or saline by intraperitoneal injection every 12 hours.

Figure 5:
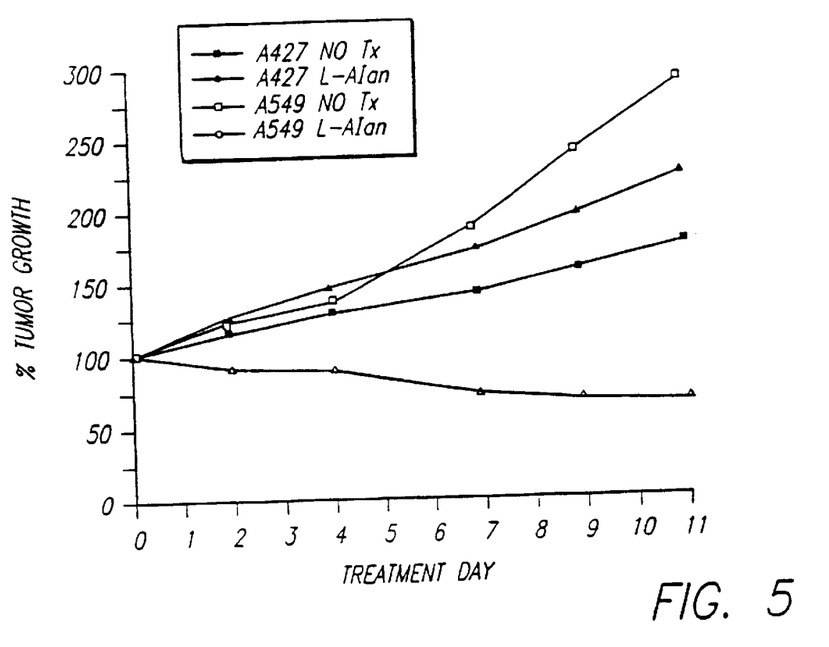
FIG. 5 is a graph representing the reduction in tumor growth acheived in MTAse deficient tumor cells in mice after daily injection of L-alanosine.

Mice received 15 mg/kg per injection for 7 days then 22.5 mg/kg for 5 days. Tumor size was measured as the product of perpendicular diameters. The results for treated (n=6 [sample size] for each cell type) vs. control (n=4 [sample size] for each cell type) mice are shown in FIG. 5.

No toxicity was evident at either dosing level tested (mice had stable weights throughout testing). L-alanosine administered by twice daily bolus injection caused a decrease in the size of well-established MTAP-deficient tumors, but had no effect on the growth of MTAP-positive cells.

SUMMARY OF SEQUENCES

SEQUENCE ID. NO.1 is the genomic clone for methylthioadenosine phosphorylase (MTAse).

What is claimed is:

1. A method for suppressing multiple drug resistance (MDR) in target cells of a vertebrate host comprising treating methylthioadenosine phosphorylase (MTAse) deficient target cells with a therapeutically effective amount of an adenine synthesis inhibitor, wherein the treatment has the effect of depleting the target cells of adenosine 5'-triphosphate, thereby suppressing MDR in the target cells.

2. The method according to claim 1, wherein the adenine synthesis inhibitor is L-alanosine.

3. The method according to claim 1, further comprising treatment of the host with a chemotherapeutic or anti-cancer agent.

4. The method according to claim 1 wherein the MTAse deficiency in target cells is determined by:
   (a) obtaining an assayable sample of target cells which are suspected of being MTAse deficient;
   (b) adding oligonucleotide probes to the sample which will specifically hybridize to any of the MTAse encoding nucleic acid present in the sample, wherein the addition is performed under conditions which will allow the probes to detectably hybridize to any such nucleic acid present in the sample; and,
   (c) detecting whether MTAse encoding nucleic acid is present in the sample, wherein the presence of said nucleic acid is indicative of the presence of MTAse protein in the sample of target cells.

5. The method according to claim 1 wherein the MTAse deficient host cells are primary tumor cells selected from the group consisting of non-small cell lung cancer cells, acute lymphoblastic leukemia cells, glioma cells and urothelial tumor cells.

6. The method according to claim 1 wherein the host is a human.

7. The method according to claim 1, wherein a substrate for intracellular production of AMP is administered to the host after treatment of the target cells with the adenine synthesis inhibitor.

8. The method according to claim 1, further comprising treatment of the host with an adenosine kinase inhibitor.

9. The method according to claim 8, wherein the adenosine kinase inhibitor is a compound has the formula:

-continued wherein
Y is CH or N;
R₁ is H or an alkyl having from 1 to 18 carbon atoms;
R₂ is an O-aroyl having from 1 to 24 carbon atoms, N₃, NH₂, NHNH₂, NHOH, OSO₂NH₂, NHOR₃, SH, SR₅, OR₄, NHR₆ or halogen;
R₃ is an O-alkyl having from 1 to 18 carbon atoms or an O-aryl having from 6 to 24 carbon atoms;
R₄ is an alkyl having from 1 to 18 carbon atoms or CN;
R₅ is an alkyl having from 1 to 18 carbon atoms or CN;
R₆ is the same as R₃, COR₃, an acyloxymethyl having from 2 to 24 carbon atoms or CONH₂;
R₇ is OH, an O-aroyl having from 6 to 24 carbon atoms or an O-aryl having from 6 to 24 carbon atoms;
R₈ is OH, an O-aroyl having from 6 to 24 carbon atoms or an O-aryl having from 6 to 24 carbon atoms; and,
R₉ is Cl, Br, I or an alkyl having from 1 to 18 carbon atoms,
or halogenated derivatives or a salt thereof.

10. The method according to claim 9, wherein the adenosine kinase inhibitor is the 5'-hydroxy form of the compound of formula (1).

11. The method according to claim 8, wherein the adenosine kinase inhibitor is a compound having the formula:

(2)

wherein
R₂ is H, OH, an O-aroyl having from 1 to 24 carbon atoms, NH₂, NHNH₂, NHOH, OSO₂NH₂, NHOR₃, SH, SR₅, OR₄, NHR₆ or halogen, wherein further R₃ is an O-alkyl having from 1 to 18 carbon atoms or an O-aryl having from 6 to 24 carbon atoms; R₄ is an alkyl having from 1 to 18 carbon atoms or CN; R₅ is an alkyl having from 1 to 18 carbon atoms or CN; and, R₆ is the same as R₃, COR₃, an acyloxymethyl having from 2 to 24 carbon atoms or CONH₂;

R₇ is an O-aroyl having from 6 to 24 carbond atoms, an O-aryl having from 6 to 24 carbon atoms, hydroxyl or SO₃;

R₈ is an O-aroyl having from 6 to 24 carbond atoms, an O-aryl having from 6 to 24 carbon atoms, hydroxyl or SO₃; provided that when R₇ is SO₃, so is R₈; and, R₁₀ is an O-alkyl having from 1 to 18 carbon atoms, an O-acyl having from 1 to 18 carbon atoms, halogen, o-tosyl or OSO₂R₁₁, wherein further R₁₁ is an alkyl having from 1 to 18 carbon atoms or an aryl having from 6 to 24 carbon atoms, or halogenated derivatives or a salt thereof.

12. The method according to claim 11, wherein the adenosine kinase inhibitor is the 5'-hydroxy form of the compound of formula (2).

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 3083 base pairs
      (B) TYPE: nucleic acid
      (C) STRANDEDNESS: single
      (D) TOPOLOGY: linear    (xi) SEQUENCE DESCRIPTION: SEQ ID NO:1:

```
CCTGGTCTCG CACTGCTCAC TCCCGCGCAG TGAGGTTGGC ACAGCCACCG CTCTGTGGCT      60

CGCTTGGTTC CCTTAGTCCC GAGCGCTCGC CCACTGCAGA TTCCTTTCCC GTGCAGACAT     120

GGCCTCTGGC ACCACCACTA CCGCCGTGAA GGTGAGATGA GCCCTCCCAG CCGCAGCGGT     180

TCGCCTGCCG GATGCCTTCN NNNNNNNNNN NNNNNNNNNN NNNNNNNNNN NNNNNNNNNN     240

NNNNNNNNNN CCTTCAAATG TTTGTTGATT TTTATGGAAG CTTTGAAAT ATTTGTTGAT      300

TGATGTTCAG TAATTTTCAG ATTTCAAAAA AATAACTAGG GCTTGGCAGG AATGGAGAAG     360

AGCATATGAA TAAATGAATT TGCTTAGAAT CTTATTTCTA ATAAAAATTA CCAAATACAA     420

TAATCTTATA TGTCTTTTTC TGCTCTTAGA TTGGAATAAT TGGTGGAACA GGCCTGGATG     480

ATCCAGAAAT TTTAGAAGGA AGAACTGAAA AATATGTGGA TACTCCATTT GGCAAGGTTA     540

ATATCCAACT TGTGGAGACA TGTTTTNNNN NNNNNNNNNN NNNNNNNNNN NNNNNNNNNN     600

TTCTCTAAGT TGTATCCTCA GACTCTTCAG ATTCCATGAG TCCTGTTGTG GTTGAACAAT     660

TATAATTTAC ATACCTGTTT TTTAAATCAC TGAGTTAAAT GTCATTTTTT TCATTGCATG     720

CAGCCATCTG ATGCCTTAAT TTTGGGGAAG ATAAAAAATG TTGATTGCGT CCTCCTTGCA     780

AGGTATGGTA NNNNNNNNNN NNNNNNNNNN NNNNNNNNNN NNNNNNNNNN NNNNNNNNNN     840

NNNNNNNNNN AAGCTTGATA CTCATCACGG GTTAACAATT TCTTCTCTCC TTCCATAGGC     900

ATGGAAGGCA GCACACCATC ATGCCTTCAA AGGTCAACTA CCAGGCGAAC ATCTGGGCTT     960

TGAAGGAAGA GGGCTGTACA CATGTCATAG TGACCACAGC TTGTGGCTCC TTGAGGGAGG    1020

AGATTCAGCC CGGCGATATT GTCATTATTG ATCAGTTCAT TGACAGGTAA GCAGTCATAC    1080

AAAATGCTTT AGGCTATTGT AGCTGGTCAT TTTCAGCTCA AATGGACGAC NNNNNNNNNN    1140

NNNNNNNNNN NNNNNNNNNN NNNNNNNNNN NNNNNNNNNN NNNNNNNNNN NNNNNNNNNN    1200

GAGGTCGACG GTATCGATAA GCTTTGTAAA CAATTGTCTT TAGCTTATCC AGAGGAATTG    1260

AGTCTGGAGT AAAGACCCAA ATATTGACCT AGATAAAGTT GACTCACCAG CCCTCGGAGG    1320

ATGGAAAGAT GGCCTTAAAA TAAAACAAAC AAAAACCTTT TTTGCTTTAT TTGTAGGAC     1380

CACTATGAGA CCTCAGTCCT TCTATGATGG AAGTCATTCT TGTGCCAGAG GAGTGTGCCA    1440

TATTCCAATG GCTGAGCCGT TTTGCCCCAA AACGAGAGAG GTGTGTAGTC TTTCTGGAAG    1500

GTGTACCAGA ATAAATCATG TGGGCTTGGG GTGGCATCTG GCATTTGGTT AATTGGCAGA    1560

CGGAGTGGCC CCATACCCTC ACTCAAGTTT GCTTTGTATT ATGCAAGTTT ATGGAGAGTT    1620

ATTTCCTGTT GCTAATAATT TNNNNNNNNN NNNNNNNNNN NNNNNNNNNN NNNNNNNNNN    1680

NNNNNNNNNN NNNNNNNNNN AAGTGCAGCC TTAAGTTGTG CATGTGCTAG TATGTTTTGA    1740

AGTTTCTGGT TTTTCTTTTC TAGGTTCTTA TAGAGACTGC TAAGAAGCTA GGACTCCGGT    1800

GCCACTCAAA GGGGACAATG GTCACAATCG AGGGACCTCG TTTTAGCTCC CGGGCAGAAA    1860
```

```
GCTTCATGTT CCGCACCTGG GGGGCGGATG TTATCAACAT GACCACAGTT CCAGAGGTGG    1920

TTCTTGCTAA GGAGGCTGGA ATTTGTTACG CAAGTATCGC CATGGGCACA GATTATGACT    1980

GCTGGAAGGA GCACGAGGAA GCAGTAGGTG GAATTCTTTT CTAAGCACAT ATAGCATGGG    2040

TTTCTGGGTG CCAATAGGGT GTCTTAACTG TTTGTTTCTA TTACGTTAGT TTCAGAAAGT    2100

GCCTTTCTAC AAGGTTTTGA AGTTGTTAAT ATTTTCTGTA GTTCCATTGG AAGGTAAGAA    2160

CAAAGATCAA AAGAAAGAAA GAGACACTTT TACCCAAGGA TCAGTAGTGA AAATAGTACA    2220

TTGTAGGCAT GTAGATGTGT TGAGAATCAT ACTAAGACTT GGGCCTTNNN NNNNNNNNNN    2280

NNNNNNNNNN NNNNNNNNNN NNNNNNNNNN NNNNNNNNNN NNNNNNNNNN NNNNNNNNNN    2340

NNNNNNNNNN GAGCTCCGAA AAATGTTTTA TGACTAGCAG TGGAATTTTA AGTTCTAGTA    2400

ACCTCCAGTG CTATTGTTTC TCTAGGTTTC GGTGGACCGG GTCTTAAAGA CCCTGAAAGA    2460

AAACGCTAAT AAAGCCAAAA GCTTACTGCT CACTACCATA CCTCAGATAG GGTCCACAGA    2520

ATGGTCAGAA ACCCTCCATA ACCTGAAGGT AAGTGTCAGC CATGGACAAC CAGGCATGTC    2580

TGGAGACTCT CTATTGTCTT CTCCTCTCAC TAGCATCACA CCCGGGGGTC CTCATGTATT    2640

TTATGCCAGC CTANNNNNNN NNNNNNNNNN NNNNNNNNNN NNNNNNNNNN NNNNNNNNNN    2700

CTGTAGAATT TATTTAAAGT GTATGTTTCC TGCGTCCTCA CTTTGATCTA GAAAATCAAA    2760

ATCTGGTTTT TTTTTTAACA AACATCTCAG TAATTACGCC AACATGTGAA TATCACTGCC    2820

TCCTTTCTTC CTTTCAGAAT ATGGCCCAGT TTTCTGTTTT ATTACCAAGA CATTAAAGTA    2880

GCATGGCTGC CCAGGAGAAA AGAAGACATT CTAATTCCAG TCATTTGGGA ATTCCTGCTT    2940

AACTTGAAAA AAATATGGGA AAGACATGCA GCTTTCATGC CCTTGCCTAT CAAAGAGTAT    3000

GTTGTAAGAA AGACAAGACA TTTGTGTGTA TTAGAGACTC CTGAATGATT TAGACAACTT    3060

CAAAATACAG AAGAAAAGCA AAA                                           3083
```